United States Patent [19]

Spence

[11] Patent Number: 4,919,888

[45] Date of Patent: Apr. 24, 1990

[54] SEALS AND METHOD OF SEALING FOR A STERILIZATION CONTAINER SYSTEM

[75] Inventor: Jerry L. Spence, Kirkland, Wash.

[73] Assignee: InstruMed, Inc., Kirkland, Wash.

[21] Appl. No.: 240,820

[22] Filed: Sep. 6, 1988

[51] Int. Cl.$^5$ .............................................. A61L 2/04
[52] U.S. Cl. ..................... 422/26; 422/300; 206/439; 206/497; 220/315; 220/359
[58] Field of Search ....................... 206/438, 439, 497; 422/26, 300; 220/315, 359; 215/232; 53/399, 421, 425, 442

[56] References Cited

U.S. PATENT DOCUMENTS

| | | | |
|---|---|---|---|
| 2,384,398 | 9/1945 | Raven | 21/91 |
| 3,252,580 | 5/1966 | Getzin | 210/485 |
| 3,259,411 | 7/1966 | Griffiths | 292/113 |
| 3,528,825 | 9/1970 | Doughty | 99/176 |
| 3,733,002 | 5/1973 | Masaaki | 215/12 R |
| 3,820,205 | 6/1974 | Shaw | 27/19 |
| 3,826,059 | 7/1974 | Novitch | 53/27 |
| 3,957,469 | 5/1976 | Nebash | 55/270 |
| 3,966,439 | 6/1976 | Vennos | 55/270 |
| 4,015,401 | 4/1977 | St Amand et al. | 53/29 |
| 4,149,650 | 4/1979 | Whelchel et al. | 220/231 |
| 4,194,622 | 3/1980 | Lewis | 206/363 |
| 4,244,920 | 1/1981 | Manschot et al. | 422/102 |
| 4,318,557 | 3/1982 | Bourne et al. | 292/113 |
| 4,331,257 | 5/1982 | Taschner | 220/324 |
| 4,349,118 | 9/1982 | Sanderson et al. | 220/201 |
| 4,358,908 | 11/1982 | Song | 47/66 |
| 4,372,921 | 2/1983 | Sanderson et al. | 422/300 |
| 4,382,808 | 5/1983 | Van Wormer, Jr. et al. | 55/418 |
| 4,416,417 | 11/1983 | Sanderson et al. | 236/92 R |
| 4,481,797 | 11/1984 | Milo | 70/167 |
| 4,487,606 | 12/1984 | Leviton et al. | 604/319 |
| 4,510,119 | 4/1985 | Hevey | 422/71 |
| 4,512,498 | 4/1985 | Leibinger | 220/371 |
| 4,514,361 | 4/1985 | Hirsch | 422/26 |
| 4,617,178 | 10/1986 | Nichols | 422/310 |
| 4,783,321 | 11/1988 | Spence | 422/300 |

FOREIGN PATENT DOCUMENTS 2289394 10/1974 France .
2375869 9/1978 France .
908407 7/1960 United Kingdom ................ 220/371

OTHER PUBLICATIONS

Portions of the Sep.-Oct. 1984 issue of the Journal of Hospital Supply, Processing, and Distribution, pp. 26-31 and Jarit ad, American ad (2p), Genesis ad, and Amsco ad (2p).

Primary Examiner—David L. Lacey
Assistant Examiner—Gregory R. Muir
Attorney, Agent, or Firm—Gregory W. Moravan

[57] ABSTRACT

At least one seal for a sterilization container system, wherein the sterilization container system comprises a base, a lid, and a gasket for providing a microorganism proof seal between the lid and the base. The seal comprises a belt of shrinkable material having an anchor at each end. Corresponding anchor openings are provided in the base of the sterilization container system for the seal's anchors. The seal is installed by engaging one of its anchors in a corresponding anchor opening on one side of the sterilization container system's base, passing its belt over the lid of the sterilization container system, and then securing its other anchor in a corresponding anchor opening on the opposite side of the sterilization container's base. The seal's belt is formed from a shrinkable material which, when exposed to a shrinking agent, shrinks to urge the sterilization container system's lid, base and gasket tightly against each other to provide a microorganism proof seal therebetween to prevent the entry of microorganisms into the interior of the sterilization container system. Also disclosed are a method of using the seal, and a method of using at least one agent which simultaneously shrinks the seal's belt and sterilizes the sterilization container system and its contents.

17 Claims, 2 Drawing Sheets

SEALS AND METHOD OF SEALING FOR A STERILIZATION CONTAINER SYSTEM

BACKGROUND OF THE INVENTION

The invention relates to seals for sterilization container systems. More particularly, it relates to new and innovative seals and methods of sealing for the same which do not involve a mechanical latching device of the type typically used on conventional sterilization container systems

SUMMARY OF THE INVENTION

A sterilization container system is a reusable device used to hold materials, such as surgical instruments, while they are being sterilized, and to keep them sterile until they are ready to be used. A typical prior art sterilization container system is a container comprising a base; a removable lid; a gasket for providing a microorganism proof seal between the base and lid; and filter means which are arranged to permit the entry of the sterilant (such as steam or ethylene oxide) into the container, but which do not permit the entry of microorganisms. The gasket is typically affixed to the lid or the base, as by a compression fit.

Since, as mentioned, one of the primary functions of a sterilization container system is to keep its sterilized contents sterile until they are needed, it is apparent that when the sterilization container system is sealed, its base, lid and gasket must be held tightly together so they do, in fact, form the desired microorganism proof seal therebetween.

Conventional prior art releasable closures for the base and lid of a conventional prior art sterilization container system are typically mechanical latching devices. Such mechanical latches suffer from numerous drawbacks. Among them are that they are relatively complex and thus they are costly to manufacture, assemble and install. They are also costly because they are likely to be made from expensive stainless steel, since stainless steel is not likely to be adversely affected by the sterilant used to sterilize the sterilization container system.

In addition, being what they are—mechanical devices—such mechanical latches are inherently subject to mechanical wear, damage, breakage and failure.

Further, such mechanical latches are typically installed on the base and lid of the sterilization container system by the use of rivets. Unfortunately, since rivets require rivet holes, it is apparent that either by improper installation or wear over time, such rivet holes may leak and permit the insidious, undetected entry of microorganisms into the sterilization container system, thereby contaminating the contents and possibly resulting in the illness or even the death of the patient upon whom the supposedly sterile contents were used. And even if the rivet holes don't leak, the wear, damage, breakage or failure of such mechanical latches could result in a poor seal between the base, lid and gasket, thereby leading to the undetected entry of microorganisms into the sterilization container system with harmful and even fatal consequences for the patient upon whom the supposedly sterile contents were used.

Further, such mechanical latches are typically provided with safety seals to provide an indication as to whether or not they have been opened, since if they are inadvertently opened prematurely the contents of the sterilization container system must be presumed to be contaminated, to be on the safe side. Such safety seals are additional expense items which are inconvenient to install and which take costly time to install. And if they are not installed because of an oversight, the result is that the sterilization container system must be presumed to have been opened and thus contaminated, necessitating the costly resterilization of the sterilization container system and its contents.

Despite all of the above disadvantages inherent with such mechanical latches for sterilization container systems, they are the typical means presently in use in the industry to releaseably seal the base, lid and gasket of a sterilization container system together.

The present invention is intended to avoid all of the above problems since it completely eliminates the need for such conventional mechanical latches to releasably seal together the base, lid and gasket of a sterilization container system.

Instead of such mechanical latches, the present invention employs at least one, and preferably two or more seals to releasably seal the base, lid and gasket of a sterilization container system together. Each seal comprises a length of conventional prior art shrinkable material, such as heat shrink polyvinyl chloride (PVC). Each seal has a pair of anchors, one at each end. For each pair of anchors, there is provided, in the sides of the base of the sterilization container system, a corresponding pair of opposed locking recesses designed to releasably engage their respective anchors. When installed on the sterilization container system, a portion of each seal passes completely over the lid of the sterilization container system.

Then, when the sterilization container system is exposed to the sterilant, such as the heat within a heat or steam based sterilizing device, the seals shrink, thereby automatically pulling the sterilization container system's base, lid and gasket together into a tight, microorganism proof seal. In addition, the seals automatically form a safety seal type indicating device since by their very presence when unbroken, they indicate the sterilized sterilization container system has not been opened or compromised.

If the sterilant is of such a nature that it will not cause the seals to shrink to the degree necessary to safely seal the sterilization container system, then prior to the sterilization container system being sterilized, the seals would be exposed to an environment suitable for causing them to shrink to the desired degree.

For example, if the seals were made from heat shrink PVC, and if it were desired to use a cold sterilizing process to sterilize the sterilization container system, then prior to the sterilizing of the sterilization container system and its contents, the installed seals would be shrunk with any convenient heat source, such as a hair dryer.

Preferably, the seals do not pass under the bottom of the sterilization container during use, thereby making them easy to install since the sterilization container system, which can be quite heavy when full of objects to be sterilized, would not have to be lifted up during the installation of the seals.

As a safety measure, each seal is preferably provided with a corresponding recess in the lid of the sterilization container system, so that during use the seal is received by its recess in the lid, thereby helping to prevent the seal from being accidentally cut or otherwise broken.

The present invention also comprises an ingenious way to secure the anchors to the seals which is quick, easy, economical and reliable. First, a large loop of shrinkable material is provided. Then the large loop of shrinkable material is flattened down so its opposite sides are touching, thereby forming a small anchor loop at each end of the flattened large loop. Next, the anchors are each inserted into a respective anchor loop, and are then secured therein by fastening together the opposite sides of the large loop closely adjacent to the anchors, so that the anchors are retained in their anchor loops by a snug friction fit.

The foregoing is intended to be but a brief summary of, not a detailed catalog of, the objects, features, advantages and characteristics of the present invention, since these and further objects, features, advantages and characteristics of the present invention will be either expressly or inherently disclosed to those of ordinary skill in the art to which it pertains, in view of the disclosures herein.

DESCRIPTION OF THE PREFERRED EMBODIMENTS

Figure 1:
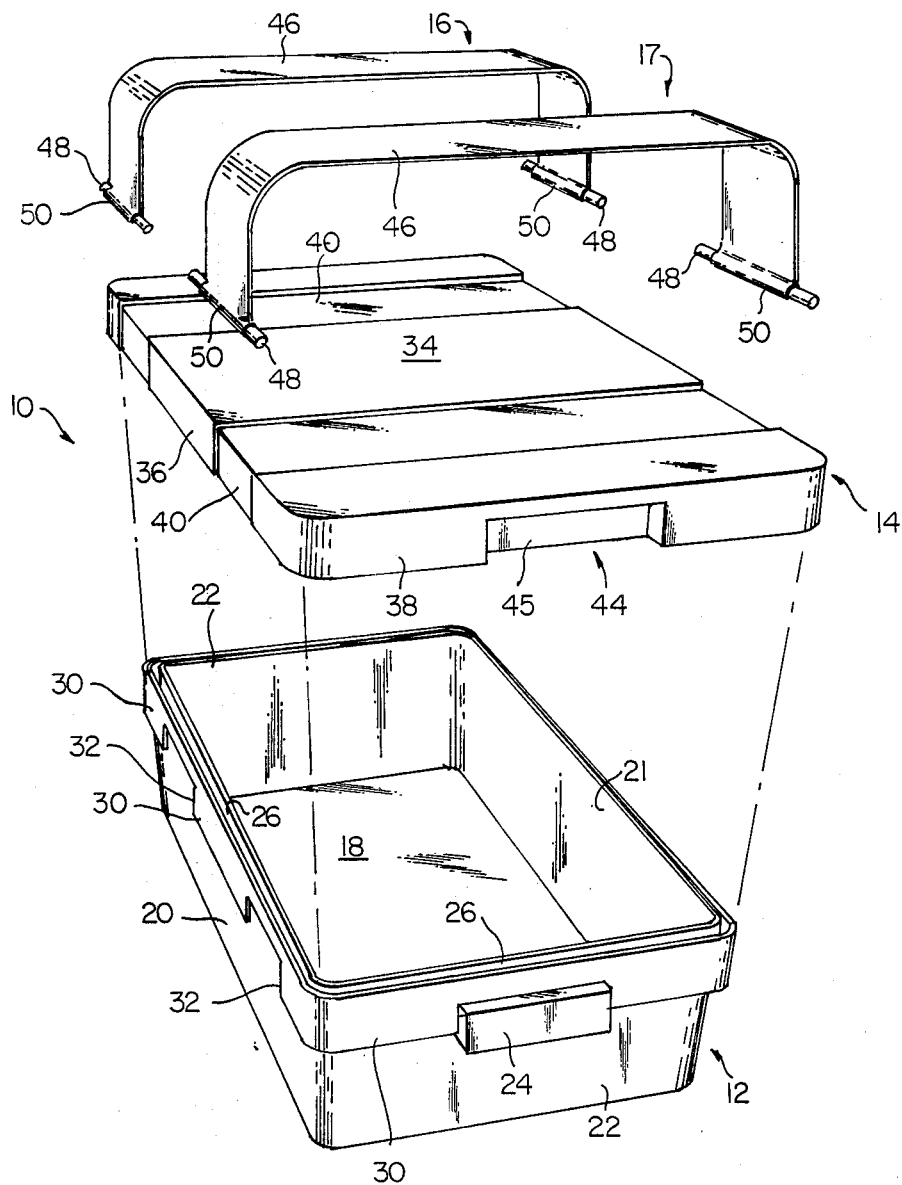
FIG. 1 is an exploded perspective view of the present invention.

Turning now to FIG. 1, it diagrammatically illustrates a sterilization container system 10 comprising a base 12 and a lid 14. As mentioned earlier, sterilization container system 10 normally includes filter means in base 12 and/or lid 14 which permit the entry and exit of sterilant into and out of sterilization container 10 while it is being sterilized, but which do not permit the entry of microorganisms into sterilization container system 10. Such filter means are not illustrated in the figures for sake of clarity since their construction and operation are entirely conventional and are well known in the art, and since they form no part, per se, of the present invention. Naturally, however, such filter means would be located in sterilization container system 10 in such a manner that they are not covered by seals 16,17 when seals 16,17 are installed on sterilization container system 10.

Figure 2:
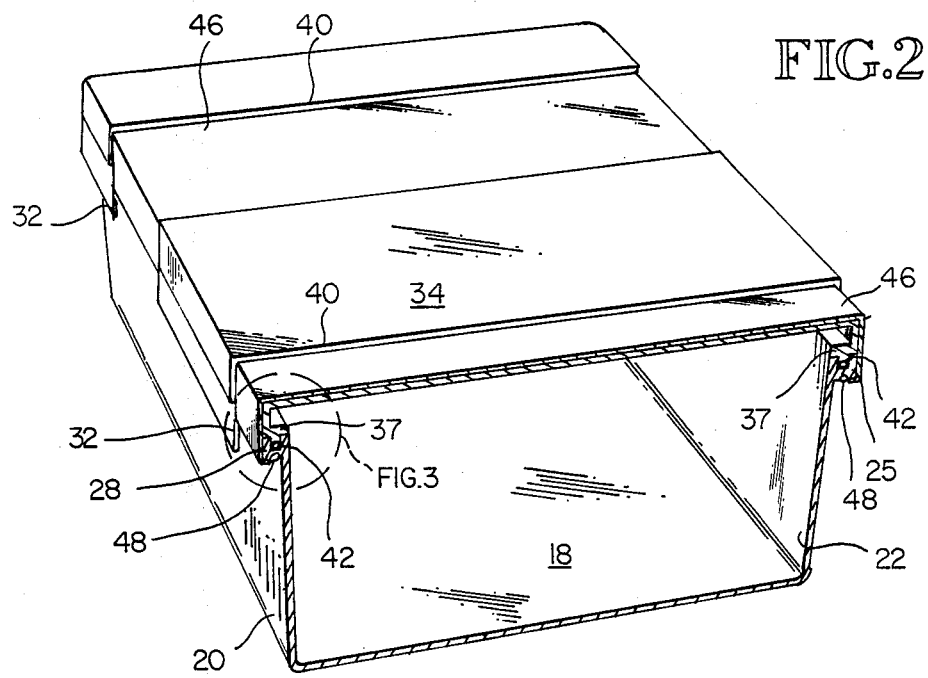
FIG. 2 is a perspective view of the present invention in operation, with one end of the sterilization container system being shown in cross section to permit viewing of some of its details of construction.
Figure 3:
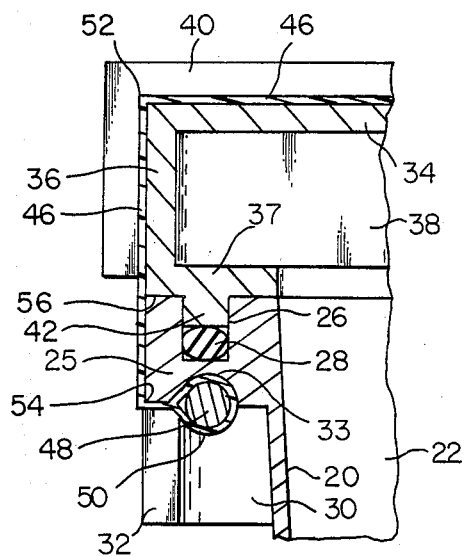
FIG. 3 is an end elevation, cross sectional view of the circled portion of the invention shown in FIG. 2.

Referring now to FIGS. 1-3, base 12 comprises a bottom wall 18; a pair of side walls 20, 21; and a pair of end walls 22, each having an outwardly projecting handle 24. Extending completely around the top of base 12 is an outwardly projecting rim 25 (see FIG. 3). Located in the top of rim 25 is a gasket channel 26 which extends completely around the top of base 12. Held in the bottom of gasket channel 26, as by a compression fit, is a gasket 28, which also extends completely around the top of base 12.

A flange 30, which projects downwardly from rim 25, extends completely around the top of base 12, except where it is interrupted by anchor openings 32. Flange 30, along with rim 25, serves to strengthen and stiffen the top portion of base 12. There are four anchor openings 32 in flange 30 on side walls 20, 21 of base 12. The two anchor openings 32 in flange 30 on side wall 20 are located opposite their two corresponding anchor openings 32 in flange 30 on side wall 21.

As best seen in FIG. 3, adjacent to each anchor opening 32 the bottom of rim 25 is provided with an anchor recess 33 which is sized to receive a corresponding anchor 48. Anchor recesses 33 are slightly longer than anchors 48, to help ensure the easy fit of anchors 48 therein.

Lid 14 comprises a top wall 34, a pair of opposed side walls 36 and a pair of opposed end walls 38. Located in top wall 34 and side walls 36 of lid 14 are a pair of seal recesses 40. As best seen in FIG. 2, seal recesses 40 are deep enough so that when seals 16, 17 are in use, their belts 46 are located within their corresponding seal recesses 40. This helps to protect belts 46 of seals 16, 17 from damage during the use and handling of sterilization container system 10.

As best seen in FIG. 3, the rim portion of lid 14 has a generally C-shaped cross section to give the rim portion of lid 14 strength and rigidity. Said rim portion of lid 14 comprises a portion of lid 14's top wall 34, lid 14's side walls 36, and rim bottom wall 37.

Extending completely around lid 14, and projecting downwardly from rim bottom wall 37, is a gasket lip 42. Gasket lip 42 is sized to be snugly received in gasket channel 26 and to seal against gasket 28 when lid 14 is sealed to base 12 in the manner which will be described below. Each end wall 38 of lid 14 includes a handle indentation 44 having a back wall 45. When lid 14 is in place on base 12, handle 44's back wall 45 is coplanar with base flange 30.

Base 12 and lid 14 may be made from any suitable strong, durable metal and/or plastic material which is not adversely affected by the sterilant or by the sterilizing conditions, such as stainless steel; aluminum; or P-1404 Noryl or P-101 polycarbonate plastic made by the General Electric Co. located in Pittsburgh, Pa. Base 12 and lid 14 are each preferably molded or formed in one piece, although they could be formed from separate components which are then assembled together, such as by gluing or by welding, in such a manner that they will not leak.

Each seal 16,17 comprises a belt 46 having an anchor 48 secured to each end thereof. Each anchor 48 is preferably a rod of stainless steel or some other strong, stiff material which is not adversely affected by the sterilant or by the sterilizing conditions, such as nylon having glass fiber filler. The length of each anchor 48 is greater than is the width of its corresponding anchor opening 32.

Each pair of anchors 48 could be secured to the ends of its respective belt 46 by any conventional means or techniques. However, it is preferred that each pair of anchors 48 be secured to its respective belt 46 by the following method, which offers the advantages of being quick, easy, economical and reliable.

First, a belt 46 is provided in the form of a large loop of strip material. The large loop of strip material is flattened down until its opposite sides are touching, thereby forming a small anchor loop 50 at each end of the flattened large loop. An anchor 48 is then inserted into each of the small anchor loops 50. Next, each anchor 48 is then secured in place in its respective anchor loop 50 with a snug friction fit by fastening together the opposite sides of the large loop which are closely adjacent to it. If belt 46 is made from heat shrink PVC, then it is prefered to do such fastening by an ultrasonic welding process. It has been found that it is preferable to tack said opposite sides together in four spaced welded locations, rather than running a continuous weld, since a continuous weld has been found to interfere somewhat with the proper shrinking of belt 46 when its respective seal 16, 17 is shrunk.

Belts 46 are preferably composed of any conventional material which shrinks under the influence of heat, such as, by way of non-limiting example, heat shrink polyvinyl chloride (PVC). But it is within the scope of the present invention that belts 46 could be composed of any one of a variety of other materials or substances which shrink under the influence of heat, or which shrink under the influence of some other shrink inducing agent such as, by way of non-limiting example, radiation, visible or invisible electromagnetic radiation, chemical(s) and/or drying. Belts 46 can be transparent, translucent or opaque.

By way of non-limiting example, if sterilization container system 10 were about two feet long, about one foot wide and about five inches thick, seals 16, 17 would be about about seventeen and one-half inches long. In addition, if belts 46 of seals 16, 17 were made of PVC, the PVC used would be about four and one-half inches wide and about three and one-half mills thick. Of course, the portions of belts 46 which are located between their small anchor loops 50 for their anchors 48 are twice as thick (seven mills). This is because if anchors 48 are secured to their belts 46 in the preferred way described above, the opposite sides of the large loop of three and one-half mill PVC material are brought into contact with each other when the large loop of PVC material is flattened to make small anchor loops 50. Thus, the total thickness of the two sides when they are brought into contact with each other is seven mills.

Prior to being shrunk, the length of each seal 16, 17 is selected so that it is just long enough, after one of its anchors 48 is received in its respective anchor recess 33, to permit its other anchor 48 to be fitted into its corresponding anchor opening 32. Thus, when seals 16, 17 are shrunk, as much of their shrinkage as is possible will go towards pulling base 12, lid 14 and gasket 28 into a tight, microorganism proof seal, rather than going towards taking up excess slack in seals 16, 17.

The width, thickness, number and material of seals 16, 17 are selected such that when seals 16, 17 are shrunk, they urge base 12, lid 14 and gasket 28 tightly against each other in a tight, microorganism proof seal. But they are not shrunk to the point where they break or might tend to break under the forces expected to be encountered during the normal handling, sterilization and storage of sterilization container system 10. Instead, their width, thickness, number and material should be selected with a substantial safety factor in mind.

Seals 16, 17, and their corresponding seal recesses 40, anchor openings 32 and anchor recesses 33 are preferably located on sterilization container system 10 so as to uniformly distribute the loading which seals 16, 17 exert on sterilization container system 10 when seals 16, 17 are shrunk, to better ensure a secure, tight, microorganism proof seal between all sealing portions of base 12, lid 14 and gasket 28.

In use, lid 14 is first placed on base 12 with its gasket lip 42 in gasket channel 26 on top of gasket 28. Then for seal 16, a first one of its anchors 48 is placed in a respective anchor opening 32 with the ends of said first anchor 48 being located behind flange 30. An upward force is exerted on said first anchor 48 by the user tugging on its respective belt 46 until said first anchor 48 is seated in its respective anchor recess 33, as best seen in FIG. 3.

Since the length of each anchor 48 is greater than is the width of its respective anchor opening 32, as long as said first anchor 48 is tugged upwardly its ends remain firmly locked in place behind flange 30.

Seal 16's belt 46 is then passed over lid 14 of sterilization container system 10. Next, seal 16's second anchor 48 is placed in its corresponding anchor opening 32. The length of seal 16's belt 46, prior to being shrunk, is short enough so that its belt 46 has to be stretched a little in order to permit the ends of seal 16's said second anchor 48 to be passed under the bottom of flange 30. Then, when said second anchor 48 is released, the elasticity of seal 16's belt 46 pulls its said second anchor 48 upwardly enough to keep it firmly in place in its respective anchor opening 32 with its ends behind flange 30, until seal 16 is shrunk. The installation of seal 17 is the same.

Next, sterilization container system 10 and its installed seals 16, 17 are inserted into the sterilization device, such as a sterilization device which utilizes steam as the sterilant. Then the same heat and temperature which is used to sterilize sterilization container system 10 and its contents will automatically act as the agent which causes the heat shrink PVC belts 46 of seals 16, 17 to shrink to the desired degree so that seals 16, 17 urge base 12, lid 14 and gasket 28 into the desired tight microorganism proof seal. When belts 46 of seals 16, 17 are fully shrunk, each anchor 48 is located in its respective anchor recess 33 as seen in FIG. 3. In order to permit belts 46 of seals 16, 17 to slide a little as they are being shrunk, and so they will not tend to be cut, corners 52 in seal recesses 40 and corners 54 on rim 25 are preferably chamfered.

In a typical steam sterilization process, steam at a temperature of 270 degrees Fahrenheit is used for at least several minutes to sterilize the sterilization container system 10 and its contents. At that temperature, the PVC belts 46 of seals 16, 17 shrink to the desired tightness in only about ten seconds, so that at the end of the sterilization cycle, sterilization container system 10 has long since been sealed by its shrunk seals 16, 17.

In general, it is preferred that the sterilant (whatever it might be) which is used to sterilize sterilization container system 10 and its contents also be used as the shrinkage inducing agent which is used to shrink belts 46 of seals 16, 17. This is highly desirable for economy, efficiency and increased ease of operation since both the sterilizing and the shrinking are then done in one step.

Alternatively, the heat or other shrinkage inducing agent could, of course be applied to seals 16, 17 before sterilization container system 10 was inserted into the sterilizing device.

When it is desired to open the sealed sterilization container system 10, belts 46 of seals 16, 17 are cut, as by passing a knife edge along seam 56 between base 12 and lid 14.

In view of the disclosures herein, various further adaptations, modifications, and uses of the present invention will now be apparent to those in the art to which it pertains, within the scope of the claims appended hereto; it being understood that all of the descriptions and figures contained herein regarding the present invention are strictly by way of non-limiting example.

What is claimed is:

1. A method of using at least one seal means for sealing a sterilization container system means, wherein said at least one seal means comprises a pair of anchor means and a belt means of shrinkable material having a pair of belt ends, wherein each of said anchor means is secured to a respective one of said belt ends;

wherein said sterilization container system means is for holding at least one object while said at least one object is being sterilized; wherein said sterilization container system means comprises a base means, a lid means and a gasket means adapted to provide a selectively releaseable seal between said base means and said lid means; wherein said base means has a bottom wall means, a pair of opposed side wall means extending upwardly from said bottom wall means, and a pair of opposed end wall means extending upwardly from said bottom wall means; wherein each of said side wall means includes an anchor engaging means for selectively engaging a respective one of said anchor means;

wherein said method comprises the steps of:
a. engaging a first one of said anchor means in a respective first one of said anchor engaging means;
b. passing said belt means across a top surface of said lid means of said sterilization container system means while said first one of said anchor means is engaged in said respective first one of said anchor engaging means;
c. engaging a second one of said anchor means in a respective second one of said anchor engaging means, while said first one of said anchor means is engaged in said respective first one of said anchor engaging means;
d. placing said sterilization container system means bearing said at least one seal means into a device for sterilizing said sterilization container system means and said at least one object;
e. exposing said sterilization container system means bearing said at least one seal means to at least one sterilizing means within said device for sterilizing until said sterilization container system means and said at least one object is sterilized and until said belt means shrinks to the point that said at least one seal means urges said base means, said lid means and said gasket means firmly together to provide a selectively releaseable microorganism proof seal between said base means, said lid means and said gasket means to prevent microorganisms from entering an interior space of said sterilization container system means; and wherein said at least one sterilizing means within said device for sterilizing acts to sterilize said sterilization container system means and said at least one object and acts to simultaneously shrink said belt means of said at least one seal means.

2. The method according to claim 1, wherein prior to step a therein, said method further comprises a method of securing said anchor means to said belt ends of said belt means, wherein said method of securing comprises the steps of:
providing said belt means in the form of a loop of said shrinkable material;
flattening said loop of shrinkable material to form a relatively flat strip of said shrinkable material having a small anchor loop means formed in each end of said relatively flat strip of said shrinkable material;
placing at least a portion of each of said anchor means within a respective one of said anchor loop means;
securing at least a portion of each of said anchor means with a snug friction fit within its said respective one of said anchor loop means by fastening together said shrinkable material in said relatively flat strip which is located closely adjacent said portion of each of said anchor means.

3. The method according to claim 1, wherein each of said anchor means comprises a strong, relatively stiff rod; and wherein said rod extends transversely with respect to said belt means.

4. The method according to claim 1, wherein each of said side walls of said sterilization container system means further comprises an outwardly projecting rim means, and a flange means extending downwardly from said rim means; wherein each of said anchor engaging means comprises an anchor opening means defined by said flange means; and wherein said anchor means are longer than the width of their corresponding said anchor opening means to enable the ends of said anchor means to be engaged by said flange means adjacent to their said corresponding said anchor opening means when said anchor means are engaged by their respective said anchor engaging means.

5. The method according to claim 1, wherein recess means for said belt means are provided in said lid means of said sterilization container system means to recess said belt means at least partially beneath an outer surface of said lid means to help to protect said belt means during use from damage.

6. The method according to claim 1, wherein at least a portion of each of said anchor means is secured with a snug friction fit within a respective anchor loop means in said belt means; wherein said belt means is a relatively flat strip which is formed from a flattened loop of said shrinkable material; and wherein said shrinkable material in said relatively flat strip which is located closely adjacent said portion of each of said anchor means is secured together to form said anchor loop means.

7. A method of using at least one seal means for sealing a sterilization container system means, wherein said at least one seal means comprises a pair of anchor means and a belt means of shrinkable material having a pair of belt ends, wherein each of said anchor means is secured to a respective one of said belt ends;

wherein said sterilization container system means is for holding at least one object while said at least one object is being sterilized; wherein said sterilization container system means comprises a base means, a lid means and a gasket means adapted to provide a selectively releaseable seal between said base means and said lid means; wherein said base means has a bottom wall means, a pair of opposed side wall means extending upwardly from said bottom wall means, and a pair of opposed end wall means extending upwardly from said bottom wall means; wherein each of said side wall means includes an anchor engaging means for selectively engaging a respective one of said anchor means;

wherein said method comprises the steps of:
a. engaging a first one of said anchor means in a respective first one of said anchor engaging means;
b. passing said belt means across a top surface of said lid means of said sterilization container system means while said first one of said anchor means is engaged in said respective first one of said anchor engaging means;

c. engaging a second one of said anchor means in a respective second one of said anchor engaging means, while said first one of said anchor means is engaged in said respective first one of said anchor engaging means;

d. exposing said sterilization container system means bearing said at least one seal means to a shrink inducing means until said belt means shrinks to the point that said at least one seal means urges said base means, said lid means and said gasket means firmly together to provide a selectively releaseable microorganism proof seal between said base means, said lid means and said gasket means to prevent microorganisms from entering an interior space of said sterilization container system means.

8. The method according to claim 7, wherein prior to step a. therein, said method further comprises a method of securing said anchor means to said belt ends of said belt means, wherein said method of securing comprises the steps of:

providing said belt means in the form of a loop of said shrinkable material;

flattening said loop of said shrinkable material to form a relatively flat strip of said shrinkable material having a small anchor loop means formed in each end of said relatively flat strip of said shrinkable material;

placing at least a portion of each of said anchor means within a respective one of said anchor loop means;

securing at least a portion of each of said anchor means with a snug friction fit within its said respective one of said anchor loop means by fastening together said shrinkable material in said relatively flat strip which is located closely adjacent said portion of each of said anchor means.

9. The method according to claim 7, wherein each of said anchor means comprises a strong, relatively stiff rod; and wherein said rod extends transversely with respect to said belt means.

10. The method according to claim 7, wherein each of said side walls of said sterilization container system means further comprises an outwardly projecting rim means, and a flange means extending downwardly from said rim means; wherein each of said anchor engaging means comprises an anchor opening means defined by said flange means; and wherein said anchor means are longer than the width of their corresponding said anchor opening means to enable the ends of said anchor means to be engaged by said flange means adjacent to their said corresponding said anchor opening means when said anchor means are engaged by their respective said anchor engaging means.

11. The method according to claim 7, wherein recess means for said belt means are provided in said lid means of said sterilization container system means to recess said belt means at least partially beneath an outer surface of said lid means to help to protect said belt means during use from damage.

12. The method according to claim 7, wherein at least a portion of each of said anchor means is secured with a snug friction fit within a respective anchor loop means in said belt means; wherein said belt means is a relatively flat strip which is formed from a flattened loop of said shrinkable material; and wherein said shrinkable material in said relatively flat strip which is located closely adjacent said portion of each of said anchor means is secured together to form said anchor loop means.

13. At least one seal means in combination with a sterilization container system means, wherein said at least one seal means comprises a pair of anchor means and a belt means of shrinkable material having a pair of belt ends, wherein each of said anchor means is secured to a respective one of said belt ends;

wherein said sterilization container system means is for holding at least one object while said at least one object is being sterilized; wherein said sterilization container system means comprises a base means, a lid means and a gasket means adapted to provide a selectively releaseable seal between said base means and said lid means; wherein said base means has a bottom wall means, a pair of opposed side wall means extending upwardly from said bottom wall means, and a pair of opposed end wall means extending upwardly from said bottom wall means; wherein each of said side wall means includes an anchor engaging means for selectively engaging a respective one of said anchor means;

wherein, during use, a first one of said anchor means is engaged in a respective first one of said anchor engaging means, a second one of said anchor means is engaged in a respective second one of said anchor engaging means, said belt means passes across a top surface of said lid means of said sterilization container system means while said first and second ones of said anchor means are engaged in their said respective first and second ones of said anchor engaging means; and wherein said belt means is shrunk to the point that said at least one seal means urges said base means, said lid means and said gasket means firmly together to provide a selectively releaseable microorganism proof seal between said base means, said lid means and said gasket means to prevent microorganisms from entering an interior space of said sterilization container system means.

14. The seal means in combination with the sterilization container system means according to claim 13, wherein each of said anchor means comprises a strong, relatively stiff rod; and wherein said rod extends transversely with respect to said belt means.

15. The seal means in combination with the sterilization container system means according to claim 13, wherein each of said side walls of said sterilization container system means further comprises an outwardly projecting rim means, and a flange means extending downwardly from said rim means; wherein each of said anchor engaging means comprises an anchor opening means defined by said flange means; and wherein said anchor means are longer than the width of their corresponding said anchor opening means to enable the ends of said anchor means to be engaged by said flange means adjacent to their said corresponding said anchor opening means when said anchor means are engaged by their said respective anchor engaging means.

16. The seal means in combination with the sterilization container system means according to claim 13, wherein recess means for said belt means are located in said lid means of said sterilization container system means to recess said belt means at least partially beneath an outer surface of said lid means to help to protect said belt means during use from damage.

17. The seal means in combination with the sterilization container system means according to claim 13, wherein at least a portion of each of said anchor means is secured with a snug friction fit within a respective anchor loop means in said belt means; wherein said belt means is a relatively flat strip which is formed from a flattened loop of said shrinkable material; and wherein said shrinkable material in said relatively flat strip which is located closely adjacent said portion of each of said anchor means is secured together to form said anchor loop means.

* * * * *